United States Patent [19]

Kirsch

[11] Plant 4,603

[45] Oct. 28, 1980

[54] LILY NAMED CRIMSON SUN

[75] Inventor: Ted T. Kirsch, Myrtle Point, Oreg.

[73] Assignee: Sun Valley Bulb Farms, Inc., Myrtle Point, Oreg.

[21] Appl. No.: 62,412

[22] Filed: Jul. 30, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct variety of chalice-type Asiatic hybrid lily plant particularly distinguished by the red-orange coloring of its medium sized, generally cupped flowers borne raceme and umbellate on short, strong stems and with upright pedicels, each pedicel usually having one or two buds or flowers. This plant also has a short, stocky growth habit with abundant and luxuriant foliage.

2 Drawing Figures

BACKGROUND OF THE NEW PLANT

This new lily was discovered by me as a seedling of unknown parentage growing among lily plants being raised at my nursery in Arcata, Calif. The short, stocky growth habit of this plant and its upright carriage of the flowers caught my attention and because of its favorable appearance, I began a course of propagation of the plant by means of scales and tissue culture at Arcata, Calif., to test its capabilities. As a result of my study, I found that this plant had other distinctive characteristics and advantages to make it a worthy addition to the field of commercial pot plant lily culture. Further asexual propagation of the plant through successive generations has demonstrated that its distinctive and advantageous characteristics hold true from generation to generation and appear to be firmly fixed.

DESCRIPTION OF THE DRAWING

My new variety of Asiatic hybrid lily is illustrated by the accompanying full color photographic drawing, which shows a full grown blooming pot plant in the upper view and a close-up view of several blooms and buds in the lower view, the color rendition being as nearly true as can be reasonably obtained by conventional photographic procedures.

DESCRIPTION OF THE NEW PLANT

The following is a detailed description of this new variety of lily based upon observations made of Arcata, Calif., the color designations being according to The R.H.S. Colour Chart published by The Royal Horticultural Society of London, England, and developed with the cooperation of the British Colour Council.

THE PLANT

Origin: Seedling.
Parentage: Unknown.
Classification:
*Botanic.*—Chalice-type, Asiatic hybrid.
*Commercial.*—Pot plant lily.
Form: Tall single stem from each bulb.
Height: 12 to 18 inches, depending upon the size of the bulb.
Growth: Upright and sturdy with excellent strength.
Cane size: The stems grow from about ¼ inch in diameter when at a height of about one foot to about ½ inch in diameter when reaching a height of about 18 inches.
Foliage: Quantity — abundant.
*Size of leaf.*—Stem leaves — about 4 inches long and ½ inch wide at the middle of the plant and from about 2 inches long and ¼ inch wide at the top of the plant. Leaves at flower cluster — 3 in number, about 1½ to 2½ inches long and about ½ to 1 inch wide.
*Shape of leaf.*—Lanceolate.
*Texture.*—Leathery.
*Aspect.*—Smooth.
Stem bulblets (under ground): Ocurrence — 4 to 12 on each healthy, normal plant at digging time.
*Size.*—About ¼ to 1 inch in diameter.
*Color.*—White.
Bulbs: Size — from 1 to 3 inches in diameter.
*Color.*—White.

THE BUD

Form: Elongate-oblong, with retuse apex.
Size: Average. 2 to 3 inches long and ½ to ⅞ inch in diameter.
Opening: Normal, with tertiary and secondary buds opening successively.
Color: Red at the tip of the bud, fading to pale orange at the base when sepals first divide and petals begin to unfurl.
Surface aspect: Pubescent, white, with hairs about 1/16 inch long.
Pedicel: Strong and generally upright and angled about 30° from vertical.
*Color.*—Light green.
*Aspect.*—Slightly pubescent with white hairs about 1/16 inch long.
*Length.*—From ¾ inch to about 2 inches.
Number of buds: 1 to 2, depending upon the size of the bulb.

THE FLOWER

Blooming habit: Annually, blooming profusely in June.
Size of flower: Medium, averaging about 4½ to 5 inches in diameter and about 1 to 1½ inch in depth.
Borne: From large bulbs, the inflorescence has a raceme arrangement for the first 2 to 6 pedicels, each with only 1 bud, and then at the top, the inflorescence breaks into an umbel cluster of 2 to 3 pedicels with 1 or 2 blooms on each pedicel. The small bulbs often flower only an umbel cluster with 1 bloom on each pedicel. The size of the bulb and its cultural care will determine the number of blooms and buds to be found in any given inflorescence. From large bulbs, this lily may have 6 to 8 blooms open at one time, 1 on each pedicel, and 1 to 2 open in the top umbel cluster.

Shape: Generally cup-shaped with uniformly spaced petals in star arrangement with the very tips of the petals folding and curving backward and under with the tip of the petal often touching the under side of the petal of a fully mature bloom.

Petalage: Normal, 3 sepals and 3 petals.

*Form.*—Oval, with retuse apex, with prominent nectariferous grooves and a center furrow bisecting each petal longitudinally. The petals are about $1\frac{1}{4}$ to $1\frac{3}{4}$ inches wide and 3 to $3\frac{1}{4}$ inches long with entire edges.

*Color.*—Upper side — upon opening, the petal is between Orange-Red RHS 33B and 33C with a white nectariferous groove extending into an area of RHS 34A at the central portion of the petal. Although not prominent, the entire petal area, including one inch of tip, is profusely covered with tiny dark spots. Under side — Pale Orange RHS 32B with the outer edges of RHS 28B. The under side is also slightly pubescent.

*Papillae.*—From 4 to 8 in number on the petals.

*Texture.*—Leathery.

*Aspect.*—Velvety.

Fragrance: Not noticeable.

Discoloration: Color fades somewhat as the blossom matures.

Effect of weather: Generally the flower is not affected by weather, but the flower ages as temperature rises.

Lasting quality: Excellent. From 3 to 6 weeks on plant, depending upon size of bulb and temperature, and from 10 days to 2 weeks as a cut flower.

Persistence: The flower tends to hang on and dry.

REPRODUCTIVE ORGANS

Stamens:

*Anthers.*—6 in number. Arrangement: orderly around pistil. Length: about $\frac{1}{2}$ inch. Color: pale orange to red at the tip.

*Filaments.*—About 2 inches long.

Pistils:

*Number.*—One.

*Style.*—About $2\frac{1}{4}$ inches long. Color: pale orange at the base becoming red at the stigma.

*Stigma.*—Color — red.

Ovary: Classified as a schizocarp, about $1\frac{1}{2}$ to 2 inches long and about 1 inch in diameter, dehiscing into thirds and containing 6 rows of seeds of the usual shape.

This new lily plant has been noted to have a very rapid asexual reproductive rate which is a distinct advantage to growers propagating this plant for the pot plant market and for cut flower production. Also, this lily plant has been found to have the ability of quick and consistently high quality response to forcing as a pot plant.

I claim:

1. A new and distinctive variety of Asiatic hybird lily plant substantially as herein shown and described, characterized by the color, form and stacked-head arrangement of its red-orange flowers; by its short and stocky growth habit and its abundant foliage; and by its rapid asexual reproductive rate and its ability for consistently high quality of forcing as a pot plant.

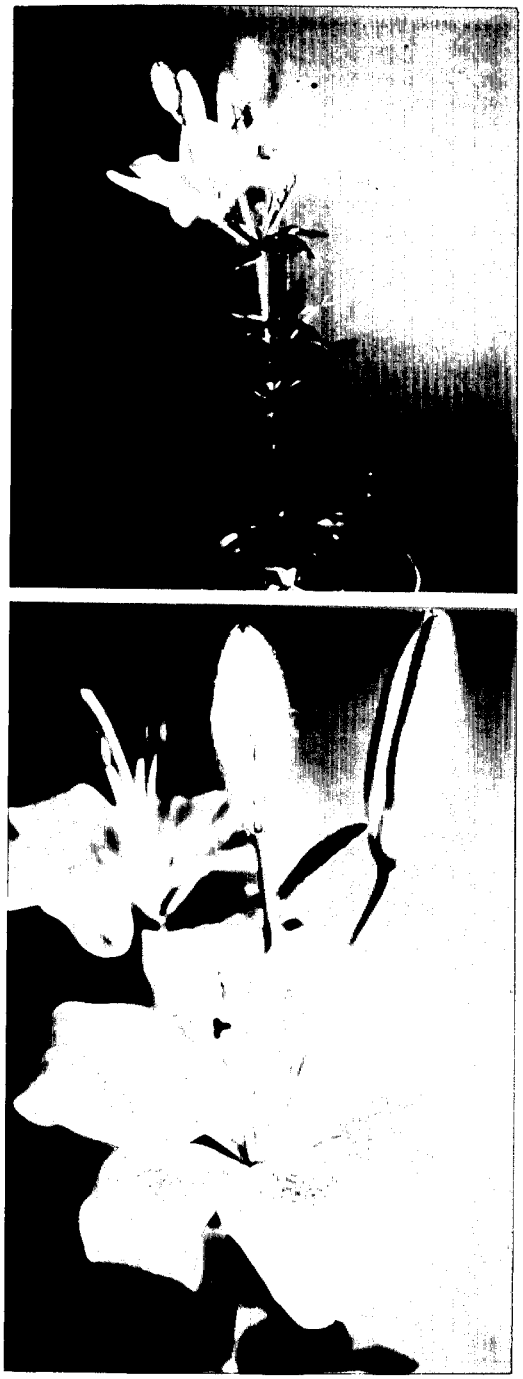

* * * * *